United States Patent [19]

Farah

[11] Patent Number: 5,217,743

[45] Date of Patent: Jun. 8, 1993

[54] BIOMATERIALS OF ENHANCED BIOCOMPATIBILITY

[75] Inventor: Salim F. Farah, Toronto, Canada

[73] Assignee: Paradigm Biotechnologies Partnership, Toronto, Canada

[21] Appl. No.: 834,137

[22] Filed: Feb. 7, 1992

[51] Int. Cl.[5] .......................... B05D 3/04; A61J 1/05
[52] U.S. Cl. ...................... 427/2; 427/400; 424/422
[58] Field of Search .................. 427/2, 400; 424/422

[56] References Cited

U.S. PATENT DOCUMENTS

| | | | |
|---|---|---|---|
| 3,865,615 | 2/1975 | Manly | 427/400 |
| 4,434,150 | 2/1984 | Azad et al. | 424/1.1 |
| 4,656,083 | 4/1987 | Hoffman et al. | 427/2 |
| 4,721,800 | 1/1988 | Chapman et al. | 556/405 |
| 4,937,369 | 6/1990 | Chapman et al. | 558/166 |
| 5,034,265 | 7/1991 | Hoffman et al. | 427/2 |
| 5,053,048 | 10/1991 | Pinchuk et al. | 427/2 |
| 5,061,750 | 10/1991 | Feijen et al. | 424/422 |
| 5,091,551 | 2/1992 | Chapman et al. | 558/166 |
| 5,122,450 | 6/1992 | Feizi et al. | 427/2 |
| 5,134,192 | 7/1992 | Feijen et al. | 427/2 |

OTHER PUBLICATIONS

Sreekumar et al, Macromolecules 22, 3303–3306 (1989).

*Primary Examiner*—Shrive Beck
*Assistant Examiner*—Erma Cameron
*Attorney, Agent, or Firm*—Timothy R. Kroboth

[57] ABSTRACT

The present invention provides a process for enhancing biomaterial biocompatibility. A biocompatibility-enhancing coating is covalently attached to a biomaterial surface through spacer arm-providing molecules previously covalently bonded to the functionalized surface. Also provided are biomaterials of enhanced biocompatibility for applications including blood oxygenator and dialyzer applications.

18 Claims, 2 Drawing Sheets

BIOMATERIALS OF ENHANCED BIOCOMPATIBILITY

BACKGROUND OF THE INVENTION

This invention relates to biomaterials of enhanced biocompatibility, in particular to a polypropylene biomaterial.

Polypropylene serves important medical and bioanalytical uses as a filtration membrane, as a gas permeable, liquid impermeable membrane in blood oxygenators, as a container for blood samples, and so forth. To improve compatibility with blood, heparin is conventionally used as an anticoagulant. However, medical and bio-analytical applications could alternatively be enhanced by improving biocompatibility of polypropylene biomaterial.

As indicated, an important use of polypropylene is as a hollow fiber membrane in blood oxygenators. Typically, blood flows externally to the hollow fiber membrane and may contact the oxygenator housing, which is commonly polycarbonate. Therefore, it would also be beneficial to improve the biocompatibility of polycarbonate biomaterial.

As illustrated by Campbell and Lyman, *Journal of Polymer Science*, 55: 169 (1961), it is known to form a chlorinated polyhydrocarbon using a chlorinating agent and white light catalysis either in a liquid reaction medium or in a gas reaction. Particularly described is chlorination of polypropylene and of poly(4-methyl-1-pentene) in a chlorinated solvent. Also described is chlorination of poly(4-methyl-1-pentene) in an aqueous suspension in which skeins of yarn of the polymer were chlorinated, and in a gas reaction in which the polymer powder was shaken in an atmosphere of chlorine gas. Surface chlorination was observed for skeins of fiber.

Also known as exemplified by Markovich et al, *Anal. Chem.* 63: 185 (1991) is the use of spacer arm chemical species such as aminopropylsilanes for covalently bonding biocompatibility-enhancing phospholipids to a silica surface, so as to provide the silica with an immobilized artificial membrane surface. The spacer armproviding molecule combines with the length of the covalently bonded acyl chain of the phospholipid to provide a sterically beneficial spacing of the phospholipid from the silica surface.

Covalent bonding of biocompatibility-enhancing compounds to polymeric substrates including polypropylene to provide biocompatible solid surfaces, is described in U.S. Pat. No. 4,973,493 to Guire. The method uses a chemical linking moiety having a reactive group for covalently bonding to the compounds, and having a photochemically reactive group for covalently binding to the polymeric substrate. The photochemical reaction is effected after the chemical linking moiety is attached to a biocompatibility-enhancing compound. As a consequence, a large steric bulk is attached to the polymeric substrate.

Problems with immobilized artificial coatings have included an insufficiently dense coverage of the biomaterial surface and non-uniformity of coverage with substantial gaps. As a result, body fluid constituents may interact with uncoated regions and with each other, with negative impact on biocompatibility.

Therefore, there remains a need for a process for enhancing biomaterial biocompatibility, and in particular for making biomaterials having improved density and uniformity of a biocompatibility-providing coating. Importantly, the artificially coated biomaterial would continue to possess beneficial physical properties of the biomaterial.

SUMMARY OF THE INVENTION

It is accordingly an object of the present invention to provide a process for enhancing biocompatibility.

It is a further object of the present invention to provide a biomaterial having an increased density of a biocompatibility-providing coating.

It is an even further object to provide a biomaterial having improved uniformity of a biocompatibility-providing coating.

It is a still further object to maintain beneficial physical properties of the biomaterial.

Additional objects, advantages and novel features of the present invention are set forth in the description that follows, and in part will become apparent to those skilled in the art upon examination of the following description or may be learned by practice of the invention. The objects and advantages of the invention may be realized and attained by means of instrumentalities and combinations particularly pointed out in the appended claims.

To achieve the foregoing objects and in accordance with the purpose of the present invention, as embodied and broadly described herein, there is provided a process for enhancing biocompatibility. By the process, surface hydrocarbons of a suitable biomaterial are reacted with a chlorinating agent under appropriate conditions to provide a biomaterial having its surface functionalized with chemically reactive moieties. The surface-functionalized biomaterial has chemically reactive moieties substituted for hydrogen atoms in a density sufficient to provide for immobilization of an artificial coating providing enhanced biocompatibility, onto the biomaterial. Substantially uniform surface distribution of the chemically reactive moieties is beneficial.

Thereafter, the surface-functionalized biomaterial is covalently bonded to spacer arm chemical species each having a functionality covalently reactive with a chemically reactive moiety of the biomaterial. The chemically reactive moieties on the biomaterial surface may be chlorine atoms or moieties derived therefrom such as hydroxyl groups. As a result, there is formed a biomaterial with spacer arm-providing molecules covalently attached.

Subsequently, a biocompatibility-enhancing coating is covalently bonded to the derivatized biomaterial via available functionalities of the spacer arm-providing molecules covalently reactive with the coating-forming compounds. In a preferred embodiment, each spacer arm-providing molecule is provided with two or more available functionalities. As a result, an increased density of the artificial coating is beneficially provided for.

BRIEF DESCRIPTION OF THE DRAWING

Reference is made to the accompanying drawing which forms a part of the specification of the present invention.

DETAILED DESCRIPTION OF THE INVENTION

Figure 1:
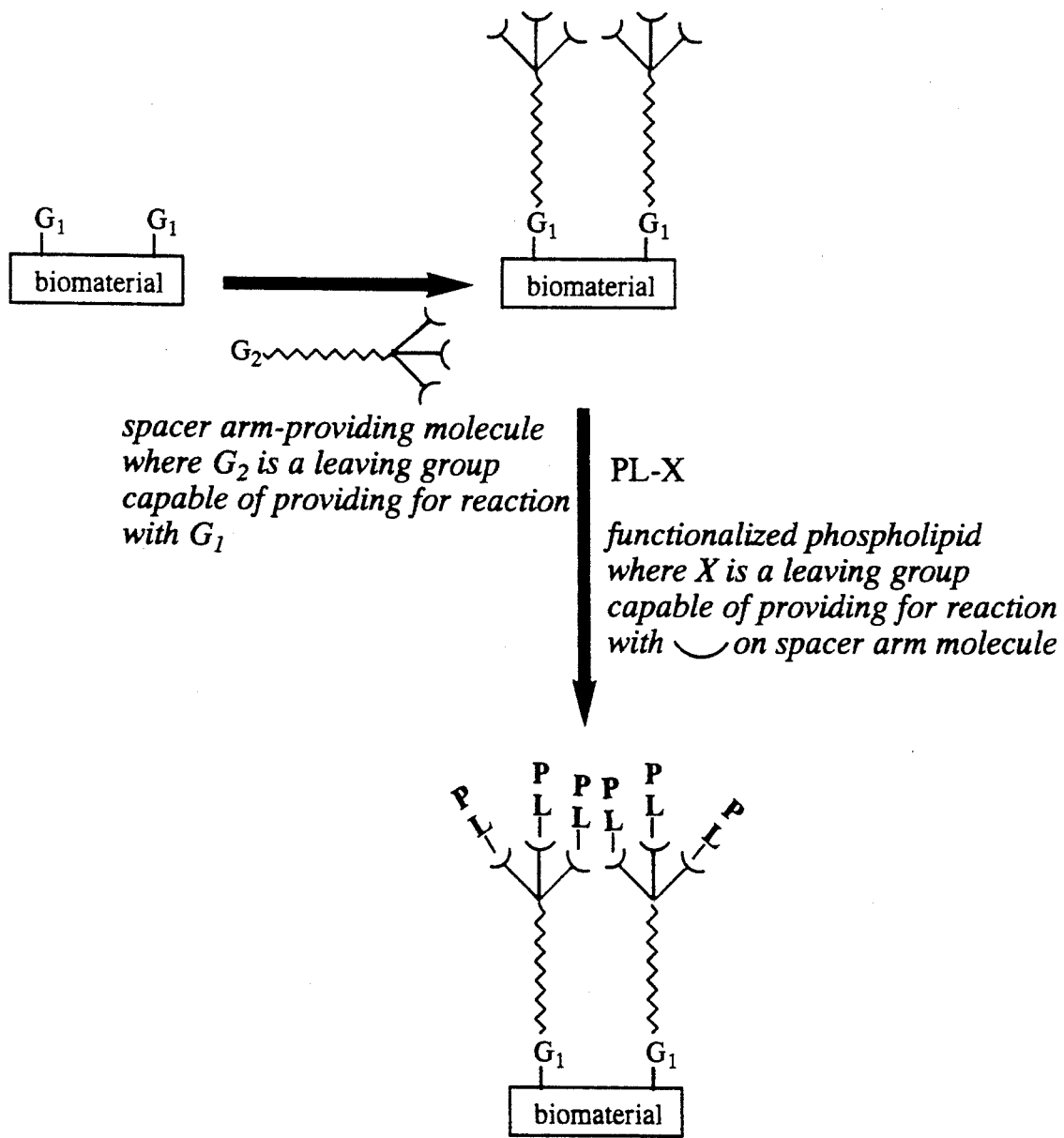
FIG. 1 depicts a reaction scheme exemplifying a preferred embodiment of the present invention.

As explained above, the present invention is directed to a process for enhancing biocompatibility, and to a biomaterial with improved density and uniformity of a biocompatibility-enhancing coating. The biomaterial may be in any of the commonly used forms such as a membrane, lens, tubular or container form. The membrane may be a filtration membrane, or in hollow fiber membrane form as in a blood oxygenator application.

Advantageously, beneficial physical properties of the biomaterial such as gas permeability and liquid impermeability in a blood oxygenator application of polypropylene biomaterial, are maintained, and the need for heparin or similar anticoagulants is reduced. An exemplary polypropylene biomaterial for use in the process of the present invention is a hollow fiber membrane with approximately 200 micron internal diameter, commercially available from Hoechst Celanese.

Enhanced biocompatibility is provided by a covalently attached coating of suitable biocompatibility-providing, chemical compounds. These chemical compounds are well known, and are exemplified by phospholipids, and anticoagulants such as heparin, urokinase, streptokinase, prostacyclin and prostacyclin derivatives. Derivatized phospholipids may be used to form a membrane layer covalently bonded to a biomaterial. Exemplary phospholipids include 1-octanoyl- and 1-hexadecanoyl-2-(8-bromooctanoyl)-sn-glycerophosphorylcholine, and the N-hydroxysuccinimidyl esters of 1-octanoyl- and 1-hexa-decanoyl-2-(8-carboxyoctanoyl)-sn-glycerophosphorylcholine. The artificial coating may contain phospholipids in combination with an anticoagulant. The density of the chemical compounds forming the artificial coating, sufficiently shields the biomaterial surface to provide the enhanced biocompatibility.

In accordance with the process of the present invention, the biomaterial surface is chemically modified, advantageously to provide thereon a substantially uniform distribution of a chemically reactive moiety. Beneficially, the remainder of the biomaterial is substantially unmodified, either chemically or physically, so as to retain beneficial physical properties. The artificial coating is covalently bonded to the chemically modified, biomaterial surface. The chemical modification forms a biomaterial surface functionalized with chemically reactive moieties such as chlorine or hydroxyl, suitable for covalent bonding to be effected.

Chemical modification of the biomaterial surface should be to a depth of no greater than about 200 Angstroms. Advantageously, the depth of surface modification is no greater than about 100 Angstroms. Accordingly, a controlled, surface selective process is needed to provide the particularly preferred, chemically modified biomaterial, in particular for providing a substantially uniform and sufficient distribution of the reactive species on the biomaterial surface, and for maintaining the underlying physical structure and beneficial physical properties.

Prior to the covalent bonding step, the biomaterial surface may be functionalized with the chemically reactive moiety at a density of from about 8 to 12 atom percent. Such a density is sufficient to provide for immobilization of a suitable artificial coating. As later described, the ability to increase the density of the artificial coating is a beneficial feature of a process in accordance with the present invention.

Covalent bonding of the artificial coating to the biomaterial surface is beneficially through a suitable spacer arm chemical species. Suitable spacer arm-providing molecules are well known, and include, but are not limited to, reactive amino moiety-containing compounds such as alkoxy- or chlorosilanes, and advantageously provide a spacer arm of sufficient length to provide the artificial coating with natural membrane-mimicking fluidity. A typical length of the spacer arm is three to fifteen atoms, but the required length for a particular application, will depend in part upon the particular atoms constituting the arm. A suitable aminoalkylsilane having displaceable alkoxy moieties is (3-aminopropyl)triethoxysilane (APTES), which has a spacer arm of six atoms length. Also suitable is 3-aminopropyldimethylethoxysilane (APDMES), which may provide a decreased percentage of coverage compared to APTES.

The spacer arm-providing molecule not only includes a first functionality covalently reactive with the chemically functionalized, biomaterial surface, but also has a second functionality for covalently bonding to the biocompatibility-providing chemical compound. When both types of covalently reactive functionalities are nucleophilic or electrophilic, the second functionality may be blocked by a conventional protective group so as to be unreactive with the chemically functionalized, biomaterial surface during covalent attachment of the spacer armproviding molecule to the biomaterial.

The spacer arm-providing molecule beneficially may include, in for example, the case of a phospholipid membrane layer, a branching side arm of roughly three to ten atoms length. Such a side arm may, in combination with the length of the phospholipid acyl chain to which it is covalently bonded, provide a sterically beneficial spacing. The acyl chain will typically be eight to twenty atoms in length. It will be of course understood that a relatively longer linking chain of the artificial coating-forming compound requires a relatively shorter, branching side arm of the spacer arm molecule to provide a sterically beneficial spacing for enhancing the artificial coating density. Furthermore, the extent of spacing sterically necessary, will depend upon the steric bulk of the chemical compounds forming the artificial coating. A further consideration is that a relatively shorter side arm may have a better orientation for covalently bonding to the artificial coating-forming compounds. Determination of the steric spacing requirement for a particular artificial coating-forming compound, is well within the capability of one skilled in the art.

In preparation for the process of the present invention, the biomaterial may be cleaned with suitable solvents to remove any surface impurities, and dried. A satisfactory sequential solvent system for a polypropylene biomaterial is chloroform, methanol and acetone.

In accordance with the process of the present invention, surface hydrocarbons of the biomaterial are beneficially functionalized with chlorine atoms. A suitable chlorinating agent such as chlorine gas, is used to provide the chlorine functionalization. In the chlorination step, hydrogen atoms of surface hydrocarbons are replaced with chlorine atoms. The tertiary hydrogens of polypropylene biomaterial are most easily replaced. The chlorination is advantageously carried out under conditions to enhance surface selectivity: the biomaterial surface is chlorine functionalized; whereas, beneficially, the remainder of the biomaterial is substantially chemically and physically unmodified.

In accordance with the process of the present invention, an oxygen-free atmosphere is beneficially provided for the chlorinating agent. When a controlled chlorination is carried out in a gas reaction with chlorine gas, suitable surface chlorination is produced. Advantageously, chlorine gas may be slowly passed through a chamber containing the biomaterial, at a chlorine flow rate of approximately one bubble every one to two seconds, as measured in a chlorine scrubber. When the chlorine flow is continued for about ten minutes under conventional white light illumination and without agitation of the biomaterial, a total chlorination of about 18 to 21 atom percent may result in the case of polypropylene biomaterial, of which about 60 to 65 percent will be on the surface, that is, about 10 to 13 atom percent chlorine, and the surface chlorination is substantially uniform. Thus, by the use of the process, modification of the biomaterial can be substantially limited to the surface, the depth of the surface modification can be limited, and substantially uniform distribution of the chemically reactive moieties can b achieved.

In the case of polypropylene biomaterial, an objective is to take advantage of, and limit the chlorination, to surface carbons having tertiary hydrogens. For polycarbonate biomaterial, chlorination involves surface carbons having primary hydrogens. As a result, a longer chlorination time is beneficial, generally about twice as long as, for instance twenty minutes compared to ten minutes, for polypropylene biomaterial. Even so, the atom percent surface chlorine may be less for polycarbonate biomaterial.

For polyacrylonitrile biomaterial, chlorination involves surface carbons having secondary carbons. Typically, chlorination of polyacrylonitrile biomaterial is roughly the same as for polycarbonate biomaterial. Polyacrylonitrile biomaterial is commonly used as a hollow fiber membrane in dialyzers.

In a beneficial application of the process, the chlorination step and steps described hereinafter, are carried out on a blood oxygenator having a polycarbonate housing and a polypropylene hollow fiber membrane so as to simultaneously surface functionalize both biomaterials. In this way, existing oxygenators may be provided with improved biocompatibility.

From the foregoing, it may be understood that a limitation on the process of the present invention is the feasibility of functionalizing the biomaterial prior to spacer arm attachment. Accordingly, a suitable biomaterial for use in the process is beneficially capable of being surface functionalized with chlorine atoms. Polyolefins such as polyethylene, polysulfone, polystyrene and polyurethane further illustrate suitable polymeric biomaterials.

In accordance with the process of the present invention, a biomaterial functionalized with chemically reactive moieties suitable for covalent bonding to be effected, is used to covalently immobilize suitable biocompatibility-enhancing compounds, beneficially by indirect attachment through the spacer arm chemical species. In such case, a stoichiometric excess of the spacer arm-providing molecule to be covalently bonded to the functionalized biomaterial, is conveniently used. Likewise, a stoichiometric excess of the biocompatibility-enhancing compounds is conveniently reacted with the spacer arm-derivatized biomaterial.

These covalent bonding reactions should be effected in a suitable solvent that is non-reactive and otherwise compatible with the reaction starting materials. Suitable organic solvents are hexane, chloroform, and methanol. Methanol should be used with an APTES-derivatized polycarbonate biomaterial. The covalent bonding reactions are beneficially carried out in an inert atmosphere, and under anhydrous conditions. Reflux conditions are suitable for covalently bonding APTES to a functionalized biomaterial, and a 50° C. reaction temperature is effective for covalently bonding a phospholipid membrane layer to the biomaterial through an APTES spacer arm. Sufficient time is permitted for reaction completion.

As can be understood, the process of the present invention, provides a chemically functionalized surface to which an artificial coating is covalently attached, with insignificant physical change in the surface morphology of the biomaterial.

In the process of the present invention, chlorine-functionalized biomaterial may be subjected to a hydrolysis step prior to the reaction with the spacer arm-providing molecule. Suitably, hydrolysis is achieved using an aqueous solution which may include a base such as sodium hydroxide. Refluxing for about two hours in an aqueous solution of about 0.1 M sodium hydroxide is typically effective in converting chlorine-functionalized polypropylene and polycarbonate biomaterials to hydroxyl-functionalized biomaterials. Hydrolysis of chlorine-functionalized polyacrylonitrile biomaterial is effected at reflux in distilled water.

When a hydrolysis step is used and a moisture-sensitive, self-polymerizable spacer arm-providing molecule such as APTES is selected, the spacer arm-derivatized biomaterial is advantageously treated for a sufficient time with a suitable solvent for removing any adsorbed, that is, not covalently attached, spacer arm-based polymer from the biomaterial surface, prior to reaction of the derivatized biomaterial with the artificial coating-forming chemical compound. In the case of a hydroxyl-functionalized, polypropylene biomaterial and APTES as the spacer arm-providing molecule, soaking the derivatized biomaterial in dichloromethane for about twenty four hours, removes adsorbed, APTES-based polymer from the biomaterial surface.

In accordance with the process of the present invention, the density of surface coverage of APTES on a polypropylene biomaterial may range from about 90 to 100 percent; whereas, a polycarbonate biomaterial may have a surface coverage on about order of about 50 to 60 percent. Removal of adsorbed spacer arm-based polymer from the biomaterial surface, beneficially may provide for density of the covalently bound, artificial coating-forming chemical compound in the range of about 30 to 60 percent in the case of phospholipid covalently bonded through a spacer arm provided by APTES.

In the process of the present invention, chlorine-functionalized biomaterial may be reacted directly with the spacer arm-providing molecule. Selection of this approach or use of an intermediate hydrolysis reaction will typically be determined by the chemical nature of the functionality of the spacer arm-providing molecule to be reacted with the functionalized biomaterial surface. In other words, for reacting an amino functionality of a spacer arm-providing molecule with a functionalized biomaterial surface, a chlorine-functionalized biomaterial would be suitable; whereas, on the other hand, for reacting an alkoxy functionality of a spacer arm-providing molecule with a functionalized biomaterial surface, a hydroxylfunctionalized biomaterial would be suitable.

Figure 2:
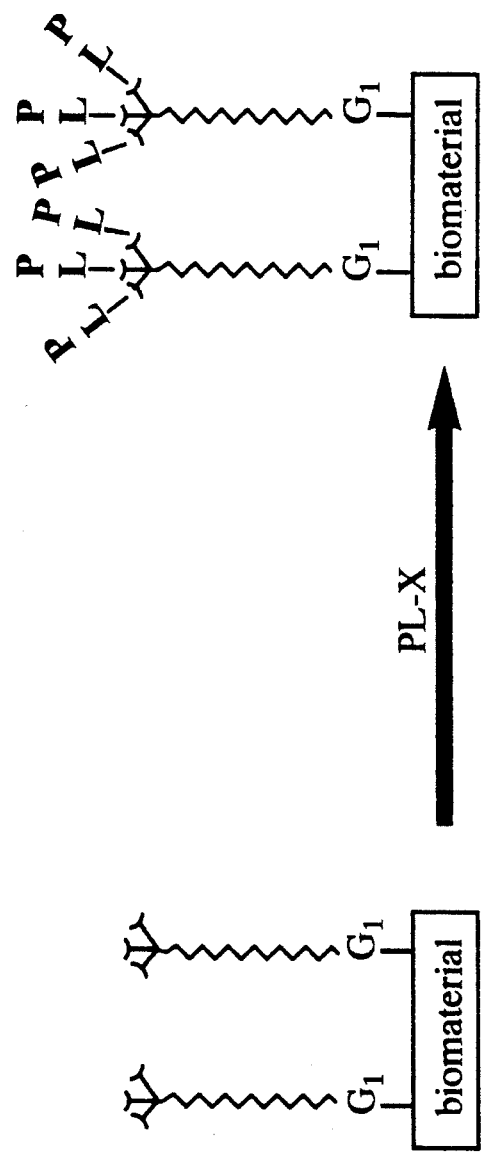
FIG. 2 depicts a reaction exemplifying a modification of the preferred embodiment of FIG. 1.

In preferred embodiment of the process, as depicted in FIGS. 1 and 2 of, a spacer arm chemical species is selected that has more than one functionality for covalently reacting with the artificial coating-forming compounds. As a result, functionalization of the biomaterial surface may be sufficient at a density of less than about eight atom percent of the chemically reactive moiety.

In this preferred embodiment, the earlier described, beneficial steric spacing takes on greater importance. Advantageously, this embodiment will produce an increased density of the biocompatibility-providing coating by providing for covalent binding of additional biocompatibility-providing compounds at a locus removed from the biomaterial surface, thereby avoiding steric hindrance at the biomaterial surface.

FIG. 1 depicts relatively longer branching side arms than are depicted in FIG. 2. The length of a branching side arm can be increased or shortened, by for instance providing a relatively greater or smaller number of methylene groups in the side arm, to maximize coverage of the artificial coating.

This preferred embodiment may be achieved by, for example, covalently bonding an APTES amino group to the functionalized, biomaterial surface. Thereafter, the three alkoxy groups of APTES may be presented for covalently binding to three molecules of the biocompatibilityproviding compound. It will be understood that this preferred embodiment can be employed with functionalized biomaterials prepared other than through a chlorination step, so as to provide increased artificial coating density.

In the Example that follows and throughout this description and the claims set forth below, all procedures are carried out at ambient temperature and pressure, unless otherwise specified.

EXAMPLE

Fifty conically-shaped, polypropylene centrifuge tubes each having a volume of 1.5 ml are sequentially cleaned with soap, distilled water, acetone, chloroform, methanol and acetone. Thereafter, the tubes are placed in a reaction flask, the flask is purged with nitrogen for about 20 minutes to avoid quenching of the chlorination reaction and provide an oxygen-free atmosphere, and under white light illumination, a controlled flow of chlorine gas is begun. The chlorine gas is passed through the flask for about ten minutes approximately at a rate of one bubble every 1 to 2 seconds, as measured in a chlorine scrubber. Thereafter, the flask is flushed with nitrogen. About 19 atom percent chlorination results, with a surface chlorination of about 11 to 12 atom percent uniformly distributed on the surface.

The resultant chlorine-functionalized, polypropylene tubes are refluxed for about two hours in an aqueous solution of 0.1 M sodium hydroxide. Then, the tubes are recovered and sequentially washed with distilled water and acetone, followed by drying.

Thereafter, the hydroxyl-functionalized, polypropylene tubes are immersed in 600 ml of dry hexane containing 12 g of freshly distilled (3-aminopropyl)triethoxysilane (APTES), several drops of triethylamine are added, and the reaction flask is purged with nitrogen. The mixture is maintained under a nitrogen blanket for 2 hours under reflux conditions, with continuous stirring. The tubes are recovered, soaked in dichloromethane for twenty four hours, sequentially washed with chloroform, methanol and acetone, and dried. As a result, the tube surface is derivatized with a spacer arm chemical species that is covalently bound thereto and that has an amino group free for covalent attachment to a compound providing enhanced biocompatibility. The tubes are estimated to have a percent surface coverage of APTES of at least about 90%.

Then, a 3.2 wt. % solution of the N-hydroxysuccinimidyl ester of 1-hexadecanoyl-2-(8-carboxyoctanoyl)-sn-glycerophosphorylcholine, in dry chloroform (25 ml) is prepared, and the APTES-derivatized tubes are added to the solution and treated at 50° C. under anhydrous conditions in a nitrogen atmosphere for 24 hours. The tubes are recovered, washed and dried. As a result, there is produced a polypropylene biomaterial of enhanced biocompatibility and having a biocompatibility-enhancing layer coated thereon and covalently bound thereto, in accordance with the present invention.

The above example is illustrative of the present invention, and is not in any way to be interpreted as limiting the scope of the invention. It will be apparent that modifications and variations are possible without departing from the scope of the invention defined in the appended claims. Several variants or modifications have been briefly mentioned for purposes of illustration.

I claim:

1. A process for enhancing biocompatibility, said process comprising reacting surface hydrocarbons of a selected polymeric biomaterial with a chlorinating agent under suitable conditions to provide a surface-activated biomaterial having chlorine atoms substituted for hydrogen atoms and directly bonded to the biomaterial surface in a density sufficient to provide for immobilization of a biocompatibility-enhancing coating; thereafter, covalently bonding the surfaceactivated biomaterial to spacer arm-providing molecules each having a first functionality covalently reactive with said surface-activated biomaterial, to produce a derivatized biomaterial with said spacer arm-providing molecules covalently attached; and thereafter, covalently bonding compounds forming said biocompatibility-enhancing coating, to said derivatized biomaterial via available covalently reactive functionalities of the attached spacer arm-providing molecules.

2. The process of claim 1, further comprising prior to the step of covalently bonding said biomaterial to said spacer arm-providing molecules, hydrolyzing chlorine atoms directly bonded to said biomaterial surface to provide a surfacehydroxylated biomaterial.

3. The process of claim 2, further comprising prior to the step of covalently bonding said compounds forming said biocompatibility-enhancing coating to the spacer armderivatized biomaterial, removing any adsorbed spacer arm-based polymer from the biomaterial surface.

4. The process of claim 1, wherein said compounds forming said biocompatibility-enhancing coating are phospholipids.

5. The process of claim 1, wherein said polymeric biomaterial is a polyolefin.

6. The process of claim 5, wherein said polyolefin is polypropylene.

7. The process of claim 1, wherein said polymeric biomaterial is a polycarbonate.

8. The process of claim 1, wherein said polymeric biomaterial is a polyurethane.

9. A process for enhancing biocompatibility, said process comprising reacting a blood oxygenator comprising polycarbonate and polypropylene biomaterials with a chlorinating agent under suitable conditions to provide surface-activated polycarbonate and polypropylene biomaterials having chlorine atoms substituted for hydrogen atoms and directly bonded to the surfaces thereof in a density sufficient to provide for immobilization of a biocompatibility-enhancing coating; thereafter, covalently bonding the surface-activated biomaterials to spacer arm-providing molecules each having a first functionality covalently reactive with said surface-activated biomaterials, to produce derivatized biomaterials with said spacer arm-providing molecules covalently attached; and thereafter, covalently bonding compounds forming said biocompatibility-enhancing coating, to said derivatized biomaterials via available covalently reactive functionalities of the attached spacer arm-providing molecules.

10. The process of claim 9, further comprising prior to the step of covalently bonding the surface-activated biomaterials to said spacer arm-providing molecules, hydrolyzing chlorine atoms directly bonded to said surfaces to provide surface-hydroxylated biomaterials.

11. The process of claim 9, wherein said compound forming said biocompatibility-enhancing coating are phospholipids.

12. A process for enhancing biocompatibility, said process comprising reacting surface hydrocarbons of a selected polymeric biomaterial with a chlorinating agent under suitable conditions to provide a surface-activated biomaterial having chlorine atoms substituted for hydrogen atoms and directly bonded to the biomaterial surface in a density sufficient to provide for immobilization of a biocompatibility-enhancing coating; thereafter, covalently bonding the surface-activated biomaterial to spacer arm-providing molecules each having a first functionality covalently reactive with said surface-activated biomaterial, to produce a derivatized biomaterial with said spacer arm-providing molecules covalently attached; and thereafter, covalently bonding compounds forming said biocompatibility-enhancing coating, to said derivatized biomaterial via available covalently reactive functionalities of the attached spacer arm-providing molecules; wherein each of said spacer arm-providing molecules has a plurality of said available covalently reactive functionalities, whereby increased density of said coating is provided for.

13. The process of claim 12, wherein each of said spacer arm-providing molecules comprises branching side arms comprising a plurality of said available covalently reactive functionalities.

14. The process of claim 12, further comprising prior to the step of covalently bonding the surface-activated biomaterial to said spacer arm-providing molecules, hydrolyzing chlorine atoms directly bonded to said biomaterial surface to provide a surface-hydroxylated biomaterial.

15. The process of claim 12, wherein said compounds forming said biocompatibility-enhancing coating are phospholipids.

16. The process of claim 12, wherein said polymeric biomaterial is a polyolefin.

17. The process of claim 16, wherein said polyolefin is polypropylene.

18. The process of claim 12, wherein said polymeric biomaterial is a polycarbonate.

* * * * *